(12) United States Patent
Ikeuchi et al.

(10) Patent No.: US 8,318,635 B2
(45) Date of Patent: *Nov. 27, 2012

(54) PHYTOTOXICITY CONTROLLING AGENT FOR UPLAND FARMING AND PHYTOTOXICITY CONTROLLING METHOD USING THE SAME

(75) Inventors: Toshihiro Ikeuchi, Tokyo (JP); Tetsuo Ohkawa, Tokyo (JP); Shuji Ohno, Tokyo (JP); Yoshihiro Yamaji, Tokyo (JP); Yasunori Ogawa, Tokyo (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 1190 days.

This patent is subject to a terminal disclaimer.

(21) Appl. No.: 12/084,482

(22) PCT Filed: Feb. 5, 2007

(86) PCT No.: PCT/JP2007/051889
§ 371 (c)(1),
(2), (4) Date: May 2, 2008

(87) PCT Pub. No.: WO2007/091502
PCT Pub. Date: Aug. 16, 2007

(65) Prior Publication Data
US 2009/0111693 A1   Apr. 30, 2009

(30) Foreign Application Priority Data

Feb. 8, 2006  (JP) ................................ 2006-031662

(51) Int. Cl.
*A01N 25/32* (2006.01)
(52) U.S. Cl. ..................................................... 504/110
(58) Field of Classification Search ................ 504/110
See application file for complete search history.

(56) References Cited

U.S. PATENT DOCUMENTS

| | | | |
|---|---|---|---|
| 3,681,045 A * | 8/1972 | Gough | 504/318 |
| 5,516,750 A | 5/1996 | Willms et al. | |
| 5,571,772 A | 11/1996 | Willms et al. | |
| 8,067,337 B2 * | 11/2011 | Ikeuchi et al. | 504/110 |
| 2005/0037922 A1 | 2/2005 | Bickers et al. | |
| 2005/0049145 A1 | 3/2005 | Bickers et al. | |
| 2006/0237685 A1 * | 10/2006 | Egawa et al. | 252/71 |
| 2006/0270557 A1 * | 11/2006 | Volgas et al. | 504/244 |
| 2007/0021303 A1 | 1/2007 | Rosinger et al. | |

FOREIGN PATENT DOCUMENTS

| | | |
|---|---|---|
| EP | 1 776 863 A1 | 4/2007 |
| JP | 10-081607 | 3/1998 |
| WO | 2005/015994 | 2/2005 |
| WO | 2005/016001 | 2/2005 |
| WO | WO 2005033362 A1 * | 4/2005 |
| WO | 2006/007892 | 1/2006 |
| WO | 2006/016527 | 2/2006 |
| WO | 2007/007629 | 1/2007 |

OTHER PUBLICATIONS

Joanna Davies "*Herbicide Safeners—Commercial Products and Tools for Agrochemical Research*", Pesticide Outlook, pp. 10-15 (Feb. 2001).

* cited by examiner

*Primary Examiner* — Robert T Crow
*Assistant Examiner* — Thor Nielsen
(74) *Attorney, Agent, or Firm* — Wenderoth, Lind & Ponack, L.L.P.

(57) ABSTRACT

It is intended to provide a phytotoxicity controlling agent usable as a herbicide for upland farming, which exerts a sufficient herbicidal effect on weeds growing together with upland crops, for example, wheat, rye, barley, oat, corn, sorghum, cotton, soybean, adzuki bean, oilseed rape, beet, upland rice and so on but causes no phytotoxic phenomenon (for example, growth inhibition, growth suppression, tiller inhibition or yellowing) in cultivated plants, comprising a nuclear-substituted benzoic acid represented by the following general formula:

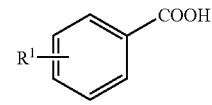

wherein $R^1$ represents linear or branched $C_{4-15}$ alkyl; a salt thereof or an alkyl ester thereof.

9 Claims, No Drawings

PHYTOTOXICITY CONTROLLING AGENT FOR UPLAND FARMING AND PHYTOTOXICITY CONTROLLING METHOD USING THE SAME

FIELD OF TECHNOLOGY

The present invention relates to a phytotoxicity-controlling agent for effectively decreasing the phytotoxicity caused when a herbicide is applied to a crop growing in a dry field as well as to a method for controlling the phytotoxicity by a herbicide for dry field cultivation by using the same.

BACKGROUND TECHNOLOGY

It is known heretofore that a great variety of herbicidal compounds exhibit a high herbicidal activity for weeds growing in a dry field such as Gramineae-family weeds, broad-leaf weeds, Cyperaceae-family weeds and the like to have a broad herbicidal spectrum.

Many of these herbicidal compounds, however, can be used with safety only for certain specific crops exhibiting phytotoxicity against other kinds of crops. Further, it may be the case even for the cultivated plants for which they can be assumedly used with safety that phytotoxicity is caused under extraordinary climatic conditions such as high temperatures, too much raining, overly humidity and others or in an environmental condition such as sandy soils or that phytotoxicity is caused when the herbicide has been applied in an excessive amount by error or by accident.

Accordingly, with regards to these herbicidal compounds, with an object to expand the coverage of the cultivated plants to which they can be applied with safety by controlling the phytotoxicity, proposals were made heretofore for a variety of phytotoxicity-controlling agents (Safeners). The activity of these phytotoxicity-controlling agents, however, is effective only for a specific herbicide applied to a specific cultivated plant and is not universally applicable.

For example, an effective phytotoxicity-controlling agent is benoxacor when metolachlor, which is a chloroacetamide-based compound, is used as a herbicide for Indian corns, is cyometrinil or fluxofenim when the same compound is used for sorghum, is fenchlorazole-ethyl when fenoxaprop-ethyl as an aryloxy phenoxypropionic acid-based herbicide is used for wheat and is mefenpyr-diethyl when the same herbicide is used for rye and barley ["Pesticide Outlook" December, 2001, pages 10-15].

When the cultivated plant is Liliiflorae, on the other hand, there are proposed insecticide-phytotoxicity controlling agents include dichlorophenylpyrazoline-3-carboxylic acid type compounds, dichlorophenylpyrazole carboxylic acid derivatives, triazole carboxylic acid type compounds, 5-benzyl or 5-phenyl-2-isoxazoline-3-carboxylic acid type compounds, 5,5-diphenyl-2-isoxazoline-3-carboxylic acid, 8-quinolinoxy acetic acid type compounds, (5-chloro-8-quinolinoxy)malonic acid type compounds, phenoxyacetic acid- or phenoxypropionic acid-derivatives type- or aromatic carboxylic acids type-active substances, pyrimidine type active substances, dichloroacetamide type active substances, dichloroacetone derivatives type active substances, oxyimino compounds type active substances, thiazolecarboxylic ester type active substances, naphthalenedicarboxylic acid derivatives type active substances, chromanacetic acid derivatives type active substances, active substances which, in addition to an insecticidal action against harmful plants, exhibit a phytotoxicity-controlling action in connection with crop plants, N-acylsulfonamide derivatives, acylsulfamoylbenzamide derivatives, dietholate, mephenate and the like (WO 2006/007982A).

DISCLOSURE OF THE INVENTION

The present invention has been completed with an object to provide a phytotoxicity-controlling agent which never causes phytotoxic syndrome such as growth inhibition, growth retardation, tillering inhibition, etiolation and the like against the cultivated plants notwithstanding a sufficient herbicidal effect against the weeds co-growing with dry-field crops such as wheat, rye, barley, oats, Indian corn, sorghum, cotton, soybean, adzuki bean, rapeseed, beet, dry-paddy rice and the like.

The inventors previously uncovered, as a phytotoxicity-controlling agent effective for paddy field crops, benzoic acid-based compounds represented by the general formula

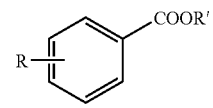

(in the formula, R denotes a hydrogen atom, an alkyl group having 1 to 15 carbon atoms, a hydroxyl group, a nitro group or an amino group and R' denotes a hydrogen atom, metal atom or an alkyl group) (WO2006-16527A) and, as a result of their further continued investigations, have found that this phytotoxicity-controlling agent is effective also for dry-field crops leading to completion of the present invention on the base of this discovery.

Thus, the present invention provides a phytotoxicity-controlling agent for weed control in dry fields comprising a nucleus-substituted benzoic acid represented by the general formula (I)

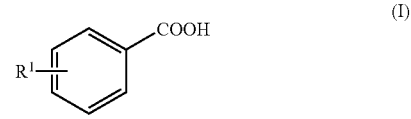

(in the formula, $R^1$ is a straight chain or branched alkyl group having 3 to 15 carbon atoms) or a salt thereof or an alkyl ester thereof as well as a method for controlling the phytotoxicity characterized in application of this phytotoxicity-controlling agent in combination with a herbicide for dry-field cultivation.

It is possible by the use of the inventive phytotoxicity-controlling agent in combination with a known herbicide for dry-field cultivation to alleviate the phytotoxicity caused by the use of the herbicide on the cultivated plants such as growth inhibition, growth retardation, tillering disorder, etiolation and others.

In the following, the present invention is described in further detail.

The phytotoxicity-controlling agent of the present invention exhibits an activity to alleviate the phytotoxicity caused on the dry-field crops by a herbicide for dry-field cultivation when used in combination with a herbicide for dry fields. The dry-field crops for which the phytotoxicity controlling effect is exhibited include any of known plants grown on non-paddy fields without particular limitations.

Examples of such plants include wheat, rye, barley, oats, Indian corn, sorghum, cotton, soybeans, adzuki beans, rapeseed, beet, dry-paddy rice and others.

While those weeds adversely affecting cultivation of those crops are removed by using a herbicide for dry fields, this herbicide is a known one described, for example, in "The Pesticide Manual" by British Crop Protection Council Co., 2004.

Such herbicides include alkaneamide-based compounds, anilide-based compounds, arylaminopropionic acid-based compounds, aryloxyalkane acid-based compounds, aryloxyphenoxy propionic acid-based compounds, benzamide-based compounds, benzenedicarboxylic acid-based compounds, benzofuran-based compounds, benzonitrile-based compounds, benzothiadiazinone-based compounds, benzothiazolone-based compounds, bipyridium-based compounds, carbamate-based compounds, thiocarbamate-based compounds, chloroacetamide-based compounds, cyclohexanedione oxime-based compounds, dinitroaniline-based compounds, diphenyl ether-based compounds, glycine-based compounds, hydroxybenzonitrile-based compounds, imidazolinone-based compounds, isoxazole-based compounds, isoxazolidinone-based compounds, N-phenylphthalimide-based compounds, oxadiazole-based compounds, oxazolidinedione-based compounds, oxyacetamide-based compounds, phenylcarbamate-based compounds, phenylpyrazole-based compounds, phenylpyridazine-based compounds, phosphinic acid-based compounds, phosphoroamidate-based compounds, phosphorodithioate-based compounds, phthalamate-based compounds, pyrazolium-based compounds, pyridazinone-based compounds, pyridine-based compounds, pyridinecarboxamide-based compounds, pyridinecarboxylic acid-based compounds, pyrimidinedione-based compounds, quinolinecarboxylic acid-based compounds, semicarbazone-based compounds, sulfonylaminocarbonyltriazolinone-based compounds, thiadiazole-based compounds, triazine-based compounds, triazinone-based compounds, triazole-based compounds, triazolinone-based compounds, triazolopyrimidine-based compounds, triketone-based compounds, uracil-based compounds, urea-based compounds, pyrimidinyloxy(thio)benzoic acid-based compounds, benzobicyclone, chlorfenac, chlorfenprop-methyl, cinmethylin, endothal, fluridon, fluorochloridon, flurtamone, indanofan, oxaziclomefone, pinoxaden, quinoclamine, thidiazimin, tridiphane, topramezon, dicamba, 2,3,6-TBA and the like.

These herbicides are available as a marketed product. For example, as the triazolopyrimidine-based compound, there are marketed cloransulam-methyl, diclosulam, flumetsulam, metosulam and the like. As the chloroacetamide-based compound, there are marketed propachlor, dimetachlor, metazachlor, thenylchlor, alachlor, acetochlor, propisochlor, S-metolachlor, dimethenamid, petoxamide and the like. As the triketone-based compound, there are marketed sulcotrione, mesotrione and the like. As the imidazolinone-based compound, there are marketed imazapyr, imazamethabenz, imazaquin, imazethapyr, imazamethapyr, imazamox and the like. As the isoxazolidinone-based compound, there is marketed clomazone. As the triazine-based compound, there are marketed ametryn, atrazine, cyanazine, dimethametryn, prometryn, propazine, simazine, simetryn, terbutylazin, terbutryn, trietazine and the like. As the aryloxyphenoxy propionic acid-based compound, there are marketed clodinafop, cyhalofop-butyl, diclofop-methyl, fenoxaprop-ethyl, fenoxaprop-P-ethyl, fenthiaprop-ethyl, fluazifop, fluazifop-P, haloxyfop, haloxyfop-P, metamifop, propaquizafop, quizalofop-ethyl, quizalofop-p-ethyl and the like. As the pyridinecarboxamide-based compound, there are marketed diflufenican, picolinafen and the like. As the alkaneamide-based compound, there are marketed diphenamid, napropamid and the like. As the anilide-based compound, there are marketed pentanochlor, propanil, naproanilide and the like. As the arylaminopropionic acid-based compound, there is marketed flamprop-M. As the aryloxyalkane acid-based compound, there is marketed MCPA-thioethyl. As the benzamide-based compound, there is marketed isoxaben. As the benzenedicarboxylic acid-based compound, there is marketed chlorthal-dimethyl. As the benzofuran-based compound, there are marketed benfuresate, ethofumesate and the like. As the benzonitrile-based compound, there is marketed dichlobenil. As the benzothiazinone-based compound, there is marketed bentazon. As the benzothiazolone-based compound, there is marketed benazolin. As the bipyridium-based compound, there are marketed diquat, paraquat and the like. As the carbamate-based compound, there are marketed asulam, carbetamide, chlorpropham, propham and the like. As the cyclohexanedione oxime-based compound, there are marketed alloxydim, butroxydim, clethodim, cycloxydim, profoxydim, sethoxydim, tepraloxydim, tralkoxydim and the like. As the dinitroaniline-based compound, there are marketed benfluralin, butralin, ethalfluralin, oryzalin, pendimethalin, trifluralin, dinitramine and the like. As the diphenyl ether-based compound, there are marketed acifluorfen, bifenox, fluoroglycofen, fomesafen, HC-252, lactofen, oxyfluorfen, aclonifen and the like. As the glycine-based compound, there are marketed glyphosate, glyphosate-trimesium and the like. As the hydroxybenzonitrile-based compound, there are marketed ioxynil, bromoxynil and the like. As the isoxazole-based compound, there is marketed isoxaflutole. As the N-phenylphthalimide-based compound, there are marketed cinidon-ethyl, flumiclorac-pentyl, flumioxazin and the like. As the oxadiazole-based compound, there are marketed oxadiargyl, oxadiazon and the like. As the oxazolidinedione-based compound, there is marketed benzoxazone. As the oxyacetamide-based compound, there are marketed flufenacet, mefenacet and the like. As the phenylcarbamate-based compound, there are marketed desmedipham, phenmedipham and the like. As the phenylpyrazole-based compound, there is marketed pyrafulfen-ethyl. As the phenylpyridazine-based compound, there is marketed pyridate. As the phosphinic acid-based compound, there are marketed bialaphos, glufosinate and the like. As the phosphoroamidate-based compound, there is marketed butamifos. As the phosphorodithioate-based compound, there is marketed bensulide. As the phthalamate-based compound, there is marketed naptalam. As the pyrazolium-based compound, there is marketed difenzoquat. As the pyridazinone-based compound, there are marketed chloridazon, flufenpyr, norflurazon and the like. As the pyridine-based compound, there is marketed dithiopyr. As the pyridinecarboxylic acid-based compound, there are marketed clopyralid, picloram, triclopyr, fluoroxypyr and the like. As the pyrimidinedione-based compound, there is marketed butafenacil. As the quinolinecarboxylic acid-based compound, there are marketed quinchlorac, quinmerac and the like. As the semicarbazone-based compound, there is marketed diflufenzopyr. As the sulfonylaminocarbonyltriazolinone-based compound, there are marketed flucarbazone-sodium, propoxycarbazone-sodium and the like. As the thiadiazole-based compound, there is marketed fluthiacet-methyl. As the triazinone-based compound, there are marketed metamitron, metribuzin and the like. As the triazole-based compound, there is marketed cafenstrole. As the triazolinone-based compound, there are marketed amicarbazone, carfentrazone-ethyl, sulfentrazone and the like. As the uracil-based compound, there is marketed lenacil. As the urea-based compound, there are marketed chlorotoluron, dimefuron, diuron, fluometuron, isoproturon, linuron, methabenzthiazuron, metobenzuron, metoxuron, neburon, benzthiazuron, cumyluron, cycluron, chloroxuron, dymron, fluothiuron, thidiazuron and the like. As the pyrimidinyloxy (thio)benzoic acid-based compound, there are marketed pyrithiobac-sodium, bispyribac-sodium and the like.

The herbicidal ingredients for which the phytotoxicity-controlling agent of the present invention can exhibit particularly preferable results, however, are the compounds represented by the general formula

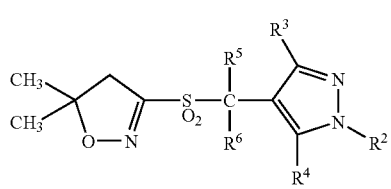

(II)

(in the formula, $R^2$ is a hydrogen atom or an alkyl group having 1 to 10 carbon atoms, $R^3$ and $R^4$ are each independently a halogen atom, an alkyl group having 1 to 10 carbon atoms, a haloalkyl group or haloalkoxy group having 1 to 4 carbon atoms and $R^5$ and $R^6$ are each independently a hydrogen atom, a halogen atom, an alkyl group having 1 to 10 carbon atoms or a haloalkyl group having 1 to 4 carbon atoms).

The phytotoxicity-controlling agent of the present invention has an activity to effectively decrease the phytotoxicity caused by the application of the aforementioned herbicides to the aforementioned dry-field crop and comprises the nucleus-substituted benzoic acid represented by the general formula (I), a salt thereof or an ester thereof as the effective ingredient.

The $R^1$ in the general formula (I) is a straight-chain or branched alkyl group having 3 to 15 carbon atoms such as n-propyl group, n-butyl group, isobutyl group, sec-butyl group, tert-butyl group, n-pentyl group, 1-methylbutyl group, n-hexyl group and the like.

Accordingly, examples of the nucleus-substituted benzoic acid represented by the general formula (I) include 4-(n-propyl)benzoic acid, 4-(n-butyl)benzoic acid, 4-isobutylbenzoic acid, 4-(tert-butyl)benzoic acid, 4-(n-hexyl)benzoic acid and the like.

As the phytotoxicity-controlling agent of the present invention, there can also be used salts of these benzoic acids or, preferably, ammonium salts and alkali metal salts or, in particular, sodium salts of these benzoic acids as well as alkyl esters thereof or, preferably, methyl 4-(n-butyl)benzoate, ethyl 4-(tert-butyl)benzoate and the like.

The phytotoxicity-controlling agent and the herbicide in the present invention are used in a mass ratio of the phytotoxicity-controlling agent to the herbicide from 50:1 to 1:2 or, preferably, from 10:1 to 1:1.

The forms of the inventive phytotoxicity-controlling agent for use include (1) a method of preparing a pesticide composition by blending a herbicidal ingredient and scattering together simultaneously, (2) a method of approximation application in which the same is applied separately from the herbicide and (3) a method of dipping foretreatment in which the crop seeds are dipped in a solution of the phytotoxicity-controlling agent prior to seeding.

When a pesticide composition for use is prepared in advance in the method (1), the phytotoxicity-controlling agent of the present invention is admixed in a prescribed proportion to a pesticide composition for conventional use followed by uniform blending. It is optional that this pesticide composition contains, besides the herbicidal ingredient and the phytotoxicity-controlling agent, other additive ingredients conventionally used in pesticide preparations according to need.

These additive ingredients include carriers such as solid carriers, liquid carriers and the like, surfactants, binders, tackifiers, thickeners, colorants, spreaders, stickers, anti-freezing agents, anticaking agents, disintegrators, stabilizers and the like.

In addition thereto, it is optional according to need that a preservative, a plant detritus and the like are used as the additional ingredient.

These additional ingredients can be used singly or can be used as a combination of two kinds or more.

The aforementioned solid carrier is exemplified, for example, by natural minerals such as quartz, clay, kaolinite, pyrophyllite, sericite, talc, bentonite, acid clay, attapulgite, zeolite, diatomaceous earth and the like; inorganic salts such as calcium carbonate, ammonium sulfate, sodium sulfate, potassium chloride and the like; organic solid carriers such as synthetic silicic acid, synthetic silicate, starch, cellulose, vegetable powders and the like; plastic carriers such as polyethylene, polypropylene, poly(vinylidene chloride) and the like; and so on. These can be used singly or can be used as a combination of two kinds or more.

The liquid carrier includes, for example, alcohols including monohydric alcohols such as methanol, ethanol, propanol, isopropanol, butanol and the like and polyhydric alcohols such as ethylene glycol, diethylene glycol, propylene glycol, hexylene glycol, poly(ethylene glycol), poly(propylene glycol), glycerol and the like; polyhydric alcohol-based compounds such as propylene glycol ether and the like; ketones such as acetone, methyl ethyl ketone, methyl isobutyl ketone, diisobutyl ketone, cyclohexanone and the like; ethers such as ethyl ether, dioxane, ethyleneglycol monoethyl ether, dipropyl ether, tetrahydrofuran and the like; aliphatic hydrocarbons such as normal paraffins, naphthenes, isoparaffins, kerosenes, minerals oil and the like; aromatic hydrocarbons such as benzene, toluene, xylene, solvent naphtha, alkylnaphthalenes and the like; halogenated hydrocarbons such as dichloroethane, chloroform, carbon tetrachloride and the like; esters such as ethyl acetate, diisopropyl phthalate, dibutyl phthalate, dioctyl phthalate, dimethyl adipate and the like; lactones such as γ-butyrolactone and the like; amides such as dimethylformamide, diethylformamide, dimethylacetamide, N-alkylpyrrolidinone and the like; nitriles such as acetonitrile and the like; sulfur compounds such as dimethyl sulfoxide and the like; vegetable oils such as soybean oil, rapeseed oil, cottonseed oil, castor oil and the like; water; and so on. These can be used singly or can be used as a combination of two kinds or more.

The surfactant includes, for example, nonionic surfactants such as sorbitan fatty acid esters, polyoxyethylene sorbitan fatty acid esters, sucrose fatty acid esters, polyoxyethylene fatty acid esters, polyoxyethylene resinate esters, polyoxyethylene fatty acid diesters, polyoxyethylene alkyl ethers, polyoxyethylene alkylphenyl ethers, polyoxyethylene dialkyl phenyl ethers, polyoxyethylene alkyl phenyl ether-formalin condensate products, polyoxyethylene-polyoxypropylene block copolymers, alkyl polyoxyethylene-polypropylene block polymer ethers, polyoxyethylenealkylamines, polyoxyethylene fatty acid amides, polyoxyethylene fatty acid bisphenyl ethers, polyalkylene benzyl phenyl ethers, polyoxyalkylene styrylphenyl ethers, acetylene diols, polyoxyalkylene-added acetylene diols, polyoxyethylene ether-type silicones, ester-type silicones, fluorine surfactants, polyoxyethylene castor oils, hydrogenated polyoxyethylene castor oils and the like; anionic surfactants such as alkyl sulfate salts, polyoxyethylene alkyl ether sulfate salts, polyoxyethylene alkyl phenyl ether sulfate salts, polyoxyethylene styryl phenyl ether sulfate salts, alkylbenzenesulfonate salts, lignin sulfonate salts, alkylsulfosuccinate salts, naphthalenesulfonate salts, alkylnaphthalene sulfonate salts, salts of formalin condensate products of naphthalene sulfonic acid, salts of formalin condensate products of alkylnaphthalene sulfonic acid, fatty acid salts, polycarboxylate salts, N-methyl-fatty acid sarcosinate, resinates, polyoxyethylene alkyl ether phosphate salts, polyoxyethylene alkyl phenyl ether phosphate salts and the like; cationic surfactants such as laurylamine hydrochloride salts, stearylamine hydrochloride salts, oleylamine hydrochloride salts, stearylamine acetate salts, stearylaminopropylamine acetate salts, alkylamine salts including alkyltrimethylammonium chloride and alkyldimethylbenzalkonium chloride and the like; ampholytic surfactants such as amino acid type- or betaine type-surfactants and the like; and so on.

These surfactants can be used singly or can be used as a combination of two kinds or more.

The binder and tackifier include, for example, carboxymethylcellulose and a salt thereof, dextrin, water-soluble starch, xanthan gum, guar gum, sucrose, poly(vinylpyrrolidone), gum arabic, poly(vinyl alcohol), poly(vinyl acetate), sodium polyacrylate, poly(ethylene glycol) with an average molecular weight of 6000 to 20000, polyethylene oxide with an average molecular weight of 100000 to 5000000, phospholipid (for example, cephalin, lecithin and the like) and so on.

The thickener includes, for example, water-soluble polymers such as xanthan gum, guar gum, carboxymethylcellulose, poly(vinylpyrrolidone), carboxyvinyl polymers, acrylic polymers, starch-based compounds and polysaccharides; inorganic fine powders such as high-purity bentonite and fumed silica (white carbon); and the like.

The colorant includes, for example, inorganic pigments such as iron oxide, titanium oxide, and Prussian blue; organic dyes such as an alizarin dye, azo dye, and metal phthalocyanine dye; and the like.

The spreader includes, for example, silicone-based surfactants, cellulose powders, dextrin, modified starch, a polyaminocarboxylic acid chelate compound, crosslinked poly(vinylpyrrolidone), a copolymer of maleic acid with a styrene compound, a (meth)acrylic acid copolymer, a half ester of a polymer composed of polyhydric alcohol with dicarboxylic anhydride, a water-soluble salt of polystyrenesulfonic acid and the like.

The sticker includes, for example, paraffin, terpene, a polyamide resin, polyacrylate, polyoxyethylene, wax, polyvinyl alkyl ether, an alkylphenol-formalin condensate product, a synthetic resin emulsion and the like.

The antifreezing agent includes, for example, polyhydric alcohols such as ethylene glycol, diethylene glycol, propylene glycol, glycerol and the like, and so on.

The anticaking agent includes, for example, polysaccharides such as starch, alginic acid, mannose, galactose and the like; poly(vinylpyrrolidone), fumed silica (white carbon), ester gum, a petroleum resin and the like.

The disintegrator includes, for example, sodium tripolyphosphate, sodium hexametaphosphate, metal stearates, a cellulose powder, dextrin, a methacrylate copolymer, poly(vinylpyrrolidone), a polyaminocarboxylic acid chelate compound, a sulfonated styrene-isobutylene-maleic anhydride copolymer, a starch-polyacrylonitrile graft copolymer and the like.

The stabilizer includes, for example, desiccants such as zeolite, calcined lime, magnesium oxide and the like; antioxidants such as phenol compounds, amine compounds, sulfur compounds, phosphoric acid compounds and the like; ultraviolet absorbers such as salicylic acid compounds, benzophenone compounds and the like; and so on.

The preservative includes, for example, potassium sorbate, 1,2-benzthiazolin-3-one and the like.

The plant detritus includes, for example, sawdust, coconut shell, corn cob, tobacco stalk and the like.

When the aforementioned additional ingredient is contained in the inventive insecticide composition, a content thereof is selected in the range of, on a mass basis, usually 5 to 95% or, preferably, 20 to 90% as a carrier, usually 0.1 to 30% or, preferably, 0.5 to 10% as a surfactant, and 0.1 to 30% or, preferably, 0.5 to 10% as other additional ingredients.

The insecticide composition can be employed as prepared in any desired formulations including liquid formulations, emulsifiable concentrates, wettable powders, dust formulations, oil solutions, water dispersible granules, flowable, emulsion waters, granules, jumbo formulations, suspo-emulsions, microcapsules and others.

During the formulation, the composition may be prepared as a mixture with pesticides other than the aforementioned components such as, for example, another herbicide, an insecticide, a fungicide, a plant growth regulator, a fertilizer and the like.

In the form preparation of these insecticide compositions, it is also optional that any one of the aforementioned formulations is in the form as wrapped with a water-soluble film. Application in this form contributes to labor saving and to attain increased safety.

This insecticide composition can be applied at any time from before incipience of weeds to the growth period thereof so as to simultaneously accomplish weed control and decrease of phytotoxicity on the cultivated plants. The cultivated plants preferably include wheat, rye, barley, oats, Indian corn, sorghum, cotton, soybean, adzuki bean, rapeseed, beet, dry-paddy rice and the like.

Further, the phytotoxicity-controlling agent of the present invention can be applied concurrently with an insecticide composition by separate form preparation from the insecticide composition containing the herbicidal ingredient or can be applied by approximation each separately.

The approximation application implied here has a meaning that the phytotoxicity-controlling agent is applied with a time interval so short as not to incur any explicit phytotoxicity on the cultivated plants by the application of a herbicidal ingredient, As to the concurrent application, it is possible that a ready-mixed form can be used so that a ready-prepared composition can be used or a form of in situ compounded form as blended a herbicidal ingredient and a phytotoxicity-controlling agent in the working site, i.e. the tank-mixed form can be applied.

The preparation method of the insecticide composition is not particularly limitative and any method optionally selected from conventional methods can be employed.

For example, a method in which a blend of all of the base materials is kneaded with addition of an appropriate volume of water followed by granulation by passing through a screen having perforations of a predetermined opening size and drying as well as a method in which a herbicidal compound, phytotoxicity-controlling agent and surfactant are dissolved or suspended in an organic solvent to be adsorbed on a carrier are applicable to the formulation.

When the insecticide composition is on use, the application dose of the herbicidal ingredient can be the same as in conventional cases without particular limitations. That is, the doses can be selected, per hectare of the field, within the ranges, usually, of: 500 to 20000 g or, preferably, 1000 to 10000 g for the alkaneamide-based compounds; 500 to 10000 g or, preferably, 1000 to 5000 g for the anilide-based compounds; 100 to 3000 g or, preferably, 200 to 2000 g for the arylaminopropionic acid-based compounds; 50 to 1000 g or, preferably, 100 to 500 g for the aryloxyalkane acid-based compounds; 5 to 2000 g or, preferably, 10 to 1000 g for the aryloxyphenoxy propionic acid-based compounds; 10 to 500 g or, preferably, 30 to 500 g for the benzamide-based compounds; 100 to 3000 g or, preferably, 500 to 2000 g for the benzenedicarboxylic acid-based compounds; 100 to 5000 g or, preferably, 200 to 3000 g for the benzofurari-based compounds; 1000 to 10000 g or, preferably, 2000 to 7000 g for the benzonitrile-based compounds; 100 to 5000 g or, preferably, 500 to 3000 g for the benzothiadiazinone-based compounds; 100 to 1000 g or, preferably, 200 to 500 g for the benzothiazolone-based compounds; 100 to 3000 g or, preferably, 200 to 2000 g for the bipyridium-based compounds; 100 to 30000 g or, preferably, 300 to 20000 g for the carbamate-based compounds; 50 to 10000 g or, preferably, 100 to 5000 g for the chloroacetamide-based compounds; 10 to 3000 g or, preferably, 20 to 2000 g for the cyclohexanedione oxime-based compounds; 100 to 10000 g or, preferably, 200 to 5000 g for the dinitoroaniline-based compounds; 50 to 5000 g or, preferably, 100 to 3000 g for the diphenyl ether-based compounds; 500 to 5000 g or, preferably, 1000 to 3000 g for the glycine-based compounds; 100 to 2000 g or, preferably, 200 to 1000 g for the hydroxybenzonitrile-based compounds; 5 to 2000 g or, preferably, 10 to 1000 g for the imidazolinone-based compounds; 10 to 500 g or, preferably, 20 to 300 g for the isoxazole-based compounds; 100 to 5000 g or, preferably, 500 to 2000 g for the isoxazolidinone-based compounds; 5 to 500 g or, preferably, 10 to 300 g for the N-phenylphthalimide-based compounds; 10 to 3000 g or, preferably, 20 to 2000 g for the oxadiazole-based compounds; 50 to 1000 g or, preferably, 100 to 500 g for the oxazolidinedione-based compounds; 100 to 3000 g or, preferably, 200 to 2000 g for the oxyacetamide-based compounds; 5 to 5000 g or, preferably, 10 to 3000 g for the phenylcarbamate-based compounds; 1 to 100 g or, preferably, 5 to 50 g for the phenylpyrazole-based compounds; 100 to 2000 g or, preferably, 500 to 1000 g for the phenylpyridazine-based compounds; 100 to 3000 g or, preferably, 300 to 2000 g for the phosphinic acid-based compounds; 100 to 3000 g or, preferably, 500 to 2000 g for the phosphoroamidate-based compounds; 1000 to 20000 g or, preferably, 2000 to 10000 g for the phosphorodithioate-based compounds; 500 to 10000 g or, preferably, 1000 to 7000 g for the phthalamate-based compounds; 100 to 5000 g or, preferably, 500 to 3000 g for the pyrazolium-based compounds; 5 to 10000 g or, preferably, 10 to 5000 g for the pyridazinone-based compounds; 5 to 500 g or, preferably, 10 to 200 g for the pyridine-based compounds; 5 to 1000 g or, preferably, 10 to 500 g for the pyridinecarboxamide-based compounds; 10 to 3000 g or, preferably, 20 to 2000 g for the pyridinecarboxylic acid-based compounds; 50 to 1000 g or, preferably, 100 to 500 g for the pyrimidinedione-based compounds; 100 to 3000 g or, preferably, 200 to 2000 g for the quinolinecarboxylic acid-based compounds; 100 to 20000 g or, preferably, 200 to 10000 g for the thiocarbamate-based compounds; 10 to 500 g or, preferably, 20 to 300 g for the semicarbazone-based compounds; 5 to 200 g or, preferably, 10 to 100 g for the sulfonylaminocarbonyltriazolinone-based compounds; 0.5 to 50 g or, preferably, 1 to 30 g for the thiadiazole-based compounds; 50 to 10000 g or, preferably, 100 to 5000 g for the triazine-based compounds; 10 to 10000 g or, preferably, 50 to 5000 g for the triazinone-based compounds; 50 to 1000 g or, preferably, 100 to 500 g for the triazole-based compounds; 0.5 to 2000 g or, preferably, 1 to 1000 g for the triazolinone-based compounds; 1 to 200 g or, preferably, 3 to 100 g for the triazolopyrimidine-based compounds; 10 to 1000 g or, preferably, 50 to 500 g for the triketone-based compounds; 50 to 10000 g or, preferably, 100 to 5000 g for the uracil-based compounds; 50 to 20000 g or, preferably, 100 to 10000 g for the urea-based compounds; 50 to 1000 g or, preferably, 100 to 500 g for benzobicyclone; 1000 to 50000 g or, preferably, 2000 to 20000 g for chlorfenac; 1000 to 10000 g or, preferably, 2000 to 5000 g for chlorfenprop-methyl; 5 to 500 g or, preferably, 10 to 300 g for cinmethylin; 500 to 20000 g or, preferably, 1000 to 10000 g for endothal; 100 to 20000 g or, preferably, 300 to 10000 g for fluridon; 100 to 2000 g or, preferably, 200 to 1000 g for fluorochloridon; 100 to 1000 g or, preferably, 200 to 500 g for flurtamone; 50 to 500 g or, preferably, 100 to 300 g for indanofan; 5 to 200 g or, preferably, 10 to 100 g for oxaziclomefone; 10 to 200 g or, preferably, 20 to 100 g for pinoxaden; 500 to 10000 g or, preferably, 1000 to 5000 g for quinoclamine; 5 to 100 g or, preferably, 10 to 50 g for thidiazimin; 50 to 2000 g or, preferably, 100 to 1000 g for tridiphane; 5 to 500 g or, preferably, 10 to 200 g for topramezon; 10 to 1000 g or, preferably, 30 to 500 g for the compounds represented by the general formula (II); 10 to 5000 g or, preferably, 50 to 1000 g for the dicamba; 100 to 20000 g or, preferably, 1000 to 10000 g for 2,3,6-TBA; and 5 to 500 g or, preferably, 10 to 200 g for pyrimidinyloxy(thio) benzoic acid.

Though not particularly limitative, the application dose of the inventive phytotoxicity-controlling agent can be selected, per hectare of the field, within the range, usually, of 10 to 5000 g or, preferably, 50 to 3000 g or, more preferably, 100 to 2000 g.

When the seeds of the cultivated plant are subjected to a dipping treatment in advance as in the method (3), the phytotoxicity-controlling agent of the present invention is dissolved in a solvent such as water to prepare a solution of a concentration of 1 to 10% by mass, in which seeds of the cultivated plant are kept immersed for 1 to 24 hours followed by sowing in a usual way.

BEST MODE TO PRACTICE THE INVENTION

In the following, the best mode to practice the present invention is described by way of Examples but the present invention is never limited thereby.

Incidentally, the "parts" and "%" in each Example are based on a mass amount unless mentioned otherwise.

Further, the active compound C in each of the Examples is a compound expressed by the formula

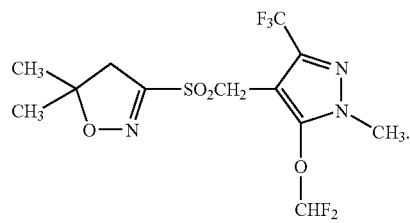

EXAMPLES 1 TO 13 AND COMPARATIVE EXAMPLES 1 TO 13

A wettable powder containing 10% of 4-(tert-butyl)benzoic acid was prepared by blending pulverization of 10 parts of 4-(tert-butyl)benzoic acid, 2 parts of a sodium salt of naphthalenesulfonic acid-formalin condensation product, 2 parts of a polyoxyethylene alkyl ether, 30 parts of diatomaceous earth and 56 parts of clay by using a high-speed air-jet pulverizer.

A wettable powder containing 10% of an active compound C was prepared by blending pulverization of 10 parts of the active compound C, 2 parts of a sodium salt of naphthalenesulfonic acid-formalin condensation product, 2 parts of a polyoxyethylene alkyl ether, 30 parts of diatomaceous earth and 56 parts of clay by using a high-speed air-jet pulverizer.

In the next place, river sand was introduced to a depth of about 1 cm onto the bottom of a 1/3000 are wide plastic container having an opening at the bottom plate and the container was filled thereon with a dry-field soil (sandy soil) followed by sowing of sweet corn (Delicious 100), wheat (Brigadier), dry-paddy rice (Labell), sorghum (Funk's Hybrid), soybean (Fukuyutaka), adzuki bean (Dainagon) or rapeseed followed by soil covering thereon in a thickness of 1 cm with the same soil. On the next day to follow sowing, a wettable dispersible granule of 80% flumetsulam (a product of Dow AgroSciences LLC, product name "Python"), a microemulsion of imazaquin ammonium salt (a product of BASF Agro Ltd. product name "Septer"), an emulsifiable concentrate of 72% dimethenamide-P (a product of BASF Agro Ltd., product name "Outlook"), a wettable powder of 100% active compound C, a water dispersible granule of 90% atrazine (a product of Syngenta Co., product name "Aa trex nine-O") and a wettable powder of 10% 4-(tert-butyl)benzoic acid were uniformly scattered individually by using a microsprayer (manufactured by Olympos Co.) with a scattering water volume of 500 liters/ha in test dose equivalents indicated in the Table and in a equivalent of 1000 g. a.i./ha, respectively. These containers were each kept standing in a water vat and water supply for pooling was introduced through the hole opening at the bottom of the water vat. After 26 days for sweet corn, wheat, dry-paddy rice, soybean, adzuki bean and rapeseed from the chemical treatment and after 11 days for sorghum from the chemical treatment, visual growth studies were conducted to evaluate the phytotoxicity indices by making comparison with the control zone where the growth had proceeded under the conditions without scattering of any herbicidal compound nor any phytotoxicity-controlling agent, i.e. 4-(tert-butyl)benzoic acid, by dividing the range from absence of growth inhibition taken as 0 and full dying of the plant taken as 100 into 100 divisions to give a numerical value for evaluation of the phytotoxicity.

For comparison, on the other hand, evaluation was made by conducting growth studies by growing sweet corn, wheat, dry-paddy rice, sorghum, soybean, adzuki bean and rapeseed under the same conditions as in the Examples excepting for the omission of scattering of 4-(tert-butyl)benzoic acid. These results are shown in Table 1.

TABLE 1

| Example | Cultivated plant | Herbicidal compound | Test dose equivalent of herbicidal compound (g ai/ha) | Test dose equivalent of 4-(tert-butyl) benzoic acid (g ai/ha) | Phytotoxicity index |
|---|---|---|---|---|---|
| Example 1 | Sweet corn | Imazaquin ammonium salt | 140 | 1000 | 10 |
| Comparative Example 1 | | Imazaquin ammonium salt | 140 | 0 | 23 |
| Example 2 | | Dimethenamide-P | 800 | 1000 | 10 |
| Comparative Example 2 | | Dimethenamide-P | 800 | 0 | 33 |
| Example 3 | | Atrazine | 1000 | 1000 | 3 |
| Comparative Example 3 | | Atrazine | 1000 | 0 | 15 |
| Example 4 | Wheat | Flumetsulam | 50 | 1000 | 5 |
| Comparative Example 4 | | Flumetsulam | 50 | 0 | 13 |
| Example 5 | | Imazaquin ammonium salt | 140 | 1000 | 5 |
| Comparative Example 5 | | Imazaquin ammonium salt | 140 | 0 | 30 |
| Example 6 | Dry-paddy rice | Imazaquin ammonium salt | 140 | 1000 | 20 |
| Comparative Example 6 | | Imazaquin ammonium salt | 140 | 0 | 50 |
| Example 7 | | Atrazine | 1000 | 1000 | 20 |
| Comparative Example 7 | | Atrazine | 1000 | 0 | 35 |
| Example 8 | Sorghum | Imazaquin ammonium salt | 140 | 1000 | 20 |
| Comparative Example 8 | | Imazaquin ammonium salt | 140 | 0 | 45 |
| Example 9 | Soybean | Imazaquin ammonium salt | 140 | 1000 | 8 |
| Comparative Example 9 | | Imazaquin ammonium salt | 140 | 0 | 15 |
| Example 10 | | Dimethenamide-P | 800 | 1000 | 10 |
| Comparative Example 10 | | Dimethenamide-P | 800 | 0 | 20 |
| Example 11 | | Active compound C | 125 | 1000 | 8 |
| Comparative Example 11 | | Active Compound C | 125 | 0 | 20 |
| Example 12 | Adzuki bean | Imazaquin ammonium salt | 140 | 1000 | 20 |
| Comparative Example 12 | | Imazaquin ammonium salt | 140 | 0 | 38 |

TABLE 1-continued

| Example | Cultivated plant | Herbicidal compound | Test dose equivalent of herbicidal compound (g ai/ha) | Test dose equivalent of 4-(tert-butyl) benzoic acid (g ai/ha) | Phytotoxicity index |
|---|---|---|---|---|---|
| Example 13 | Rapeseed | Imazaquin ammonium salt | 140 | 1000 | 25 |
| Comparative Example 13 | | Imazaquin ammonium salt | 140 | 0 | 50 |

EXAMPLES 14 TO 31 AND COMPARATIVE EXAMPLES 14 TO 31

A river sand was taken to a depth of about 1 cm on the bottom of a 1/3000 are wide plastic container having a hole in the bottom plate and the container was filled thereon with a dry-field soil (sandy soil) followed by sowing of sweet corn (Delicious 100), wheat (Brigadier), barley (Minori Rokujo), dry-paddy rice (Labell), sorghum (Funk's Hybrid), soybean (Fukuyutaka), adzuki bean (Dainagon), rapeseed or beet (VIGIL) followed by soil covering thereon in a thickness of 1 cm with the same soil. These containers were each kept standing on a water vat filled with a water pool from which water was supplied through the opening in the bottom. After 14 days from sowing when the sweet corn had grown to the 1.5 leaves stage, wheat and barley had grown to the 2 leaves stage, respectively, dry-paddy rice had grown to the 0.8 leaves stage, soybean, adzuki bean and beat had grown to the true leaf extraction stage, respectively, and rapeseed had grown to the two paired leaves extraction stage, a flowable of 7.5% fenoxaprop-P-ethyl (a product of Bayer CropScience Co., product name "Whip"), a flowable of 10% bispyribac-sodium (a product of KUMIAI CHEMICAL CO., product name "Nominee 100SC"), an emulsifiable concentrate of 72% dimethenamide-P (a product of BASF Agro Ltd., product name "Outlook"), a wettable powder of 10% active compound C, a flowable of 48% mesotrione (a product of Syngenta Co., product name "Callisto"), a wettable powder of 10% diflufenican and a wettable powder of 10% 4-(tert-butyl) benzoic acid were uniformly scattered individually by using a microsprayer (manufactured by Olympos Co.) each in test dose equivalents indicated in the Tables and in an equivalent of 1000 g a.i./ha with a scattering water volume of 500 liters/ha [addition of 0.1% of a surfactant WK (a product by Maruwa Biochemical Co.) per the solution for application]. After 8 days from the chemical treatment and after 14 days from the chemical treatment, visual growth studies were conducted for sweet corn, sorghum and adzuki bean and for wheat, barley, dry-paddy rice, soybean, rapeseed and beet, respectively and the results are shown in Table 2 and Table 3.

For comparison, on the other hand, sweet corn, wheat, barley, dry-paddy rice, sorghum, soybean, adzuki bean, rapeseed and beet were cultivated under the same conditions as in the Examples excepting for omission of scattering of 4-(tert-butyl)benzoic acid and the growth thereof was examined for evaluation. These results are shown in Table 2 and Table 3.

TABLE 2

| Example | Cultivated plant | Herbicidal compound | Test dose equivalent of herbicidal compound (g ai/ha) | Test dose equivalent of 4-(tert-butyl) benzoic acid (g ai/ha) | Phytotoxicity index |
|---|---|---|---|---|---|
| Example 14 | Sweet corn | Bispyribac-sodium | 40 | 1000 | 20 |
| Comparative Example 14 | | Bispyribac-sodium | 40 | 0 | 45 |
| Example 15 | | Dimethenamide-P | 800 | 1000 | 10 |
| Comparative Example 15 | | Dimethenamide-P | 800 | 0 | 20 |
| Example 16 | | Mesotrione | 200 | 1000 | 3 |
| Comparative Example 16 | | Mesotrione | 200 | 0 | 13 |
| Example 17 | | Diflufenican | 200 | 1000 | 15 |
| Comparative Example 17 | | Diflufenican | 200 | 0 | 35 |
| Example 18 | Wheat | Fenoxaprop-P-ethyl | 32 | 1000 | 13 |
| Comparative Example 18 | | Fenoxaprop-P-ethyl | 32 | 0 | 40 |
| Example 19 | | Bispyribac-sodium | 40 | 1000 | 20 |
| Comparative Example 19 | | Bispyribac-sodium | 40 | 0 | 35 |
| Example 20 | | Active compound C | 125 | 1000 | 5 |
| Comparative Example 20 | | Active compound C | 125 | 0 | 20 |
| Example 21 | | Mesotrione | 200 | 1000 | 20 |
| Comparative Example 21 | | Mesotrione | 200 | 0 | 40 |
| Example 22 | | Diflufenican | 200 | 1000 | 8 |
| Comparative Example 22 | | Diflufenican | 200 | 0 | 15 |

TABLE 3

| Example | Cultivated plant | Herbicidal compound | Test dose equivalent of herbicidal compound (g ai/ha) | Test dose equivalent of 4-(tert-butyl) benzoic acid (g ai/ha) | Phytotoxicity index |
|---|---|---|---|---|---|
| Example 23 | Barley | Active compound C | 125 | 1000 | 5 |
| Comparative Example 23 | | Active compound C | 125 | 0 | 18 |
| Example 24 | Dry-paddy rice | Bispyribac-sodium | 40 | 1000 | 8 |
| Comparative Example 24 | | Bispyribac-sodium | 40 | 0 | 18 |
| Example 25 | Soybean | Dimethenamide-P | 800 | 1000 | 8 |
| Comparative Example 25 | | Dimethenamide-P | 800 | 0 | 15 |
| Example 26 | | Diflufenican | 200 | 1000 | 20 |
| Comparative Example 26 | | Diflufenican | 200 | 0 | 30 |
| Example 27 | Adzuki bean | Active compound C | 125 | 1000 | 15 |
| Comparative Example 27 | | Active compound C | 125 | 0 | 25 |
| Example 28 | | Diflufenican | 200 | 1000 | 20 |
| Comparative Example 28 | | Diflufenican | 200 | 0 | 35 |
| Example 29 | Rapeseed | Dimethenamide-P | 800 | 1000 | 0 |
| Comparative Example 29 | | Dimethenamide-P | 800 | 0 | 10 |
| Example 30 | | Active compound C | 125 | 1000 | 25 |
| Comparative Example 30 | | Active compound C | 125 | 0 | 40 |
| Example 31 | Beet | Dimethenamide-P | 800 | 1000 | 20 |
| Comparative Example 31 | | Dimethenamide-P | 800 | 0 | 35 |

It is understood from Tables 1 to 3 that, as compared with the respective Comparative Examples where a phytotoxicity-controlling agent was not scattered, the phytotoxicity such as growth inhibition could be reduced in the Examples where the phytotoxicity-controlling agent was scattered. Accordingly, it is now possible by the present invention to apply insecticide compositions containing a wide range of herbicidal compound which can be applied to the crops which is hardly applicable to the treatment with the prior art herbicidal composition alone or under unfavorable conditions of ready occurrence of phytotoxicity by providing wider selection of the herbicidal compounds to a variety of crops.

In the next place, formulation examples are shown as the Reference Examples of the insecticide compositions containing the inventive phytotoxicity-controlling agent.

REFERENCE EXAMPLE 1

A wettable powder containing an active compound C and 4-(tert-butyl)benzoic acid was prepared by blending pulverization of 10 parts of the active compound C, 50 parts of 4-(tert-butyl)benzoic acid, 2 parts of a sodium salt of naphthalenesulfonic acid-formalin condensation product, 2 parts of a polyoxyethylene alkyl ether, 10 parts of diatomaceous earth and 26 parts of clay by using a high-speed air-jet pulverizer.

REFERENCE EXAMPLE 2

A wettable powder containing diflufenican and 4-(n-propyl)benzoic acid was prepared by blending pulverization of 10 parts of diflufenican, 50 parts of 4-(n-propyl)benzoic acid, 2 parts of a sodium salt of naphthalenesulfonic acid-formalin condensation product, 2 parts of a polyoxyethylene alkyl ether, 10 parts of diatomaceous earth and 26 parts of clay by using a high-speed air-jet pulverizer.

REFERENCE EXAMPLE 3

A flowable containing atrazine and 4-(n-butyl)benzoic acid was prepared by blending pulverization of 20 parts of atrazine, 20 parts of 4-(n-butyl)benzoic acid, 5 parts of a sodium salt of polyoxyethylene styryl phenyl ether sulfate, 10 parts of a propylene glycol, 0.2 part of xanthan gum and 44.8 parts of water with a wet-process pulverizer using glass beads as a pulverizing medium.

REFERENCE EXAMPLE 4

A wettable powder containing bispyribac-sodium and 4-(tert-butyl)benzoic acid was prepared by blending pulverization of 5 parts of bispyribac-sodium, 25 parts of 4-(tert-butyl)benzoic acid, 3 parts of a sodium salt of alkylnaphthalene sulfonate, 2 parts of a sodium salt of lignin sulfonate, 20 parts of diatomaceous earth and 45 parts of clay by using an impact mill.

REFERENCE EXAMPLE 5

A water dispersible granule containing an active compound C and sodium 4-(tert-butyl)benzoate was prepared by kneading a blend of 10 parts of the active compound C, 30 parts of sodium 4-(tert-butyl)benzoate, 3 parts of a sodium salt of naphthalenesulfonic acid-formalin condensation product, 5 parts of a sodium salt of lignin sulfonate, 15 parts of diatomaceous earth and 37 parts of clay with addition of an appropriate volume of water followed by extrusion granulation by passing through a screen having a 0.6 mm mesh opening diameter using an extrusion granulator followed by drying in a fluidized-bed dryer at a material temperature of 60° C. and then screening.

REFERENCE EXAMPLE 6

A water dispersible granule containing an active compound C and 4-(n-hexyl)benzoic acid was prepared by kneading a blend of 10 parts of the active compound C, 40 parts of 4-(n-hexyl)benzoic acid, 3 parts of a sodium salt of naphthalenesulfonic acid-formalin condensation product, 5 parts of a sodium salt of lignin sulfonate, 15 parts of diatomaceous earth and 27 parts of clay with addition of an appropriate volume of water followed by extrusion granulation by passing through a screen having a 0.6 mm mesh opening diameter using an extrusion granulator followed by drying in a fluidized-bed dryer at a material temperature of 60° C. and then screening.

Industrial Utilizability

The phytotoxicity-controlling agent of the present invention, being capable of effectively controlling the phytotoxicity such as growth retardation, growth inhibition, tillering inhibition, etiolation and the like caused in a great variety of dry-field crops by a wide range of herbicides, can be applied even to a cultured plant to which the prior art phytotoxicity-controlling agents are inapplicable due to their narrow applicability ranges.

Accordingly, the phytotoxicity-controlling agent of the present invention can be applied with a wide variety of herbicidal compounds in the case of their single use alone, even for those which cause the phytotoxic syndromes such as growth retardation, growth inhibition, tillering inhibition, etiolation and the like against objective crops including wheat, rye, barley, oats, Indian corn, sorghum, cotton, soybean, adzuki bean, rapeseed, beet, dry-paddy rice and the like by a method (1) in which an insecticide composition is prepared by blending with a herbicidal ingredient for simultaneous sprinkling, by a method (2) in which preparation is made separately from the herbicide for proximity application or by a method (3) in which sowing is preceded by in advance dipping of the crop seeds in a solution of the phytotoxicity-controlling agent, whereby the weed controlling effect can be fully exhibited along with a decrease or prevention of the phytotoxic syndromes appearing in the objective crops. Therefore, it is useful as an auxiliary herbicidal agent for the objective crops to which the phytotoxic syndromes can be decreased or prevented.

A further advantage is that the applicability situations can be expanded since the phytotoxicity can be decreased or prevented even to those crops to which application can heretofore be hardly performed due to low selectivity.

The invention claimed is:

1. A phytotoxicity-controlling composition for weed control in a dry field which comprises an o- or p-substituted benzoic acid compound represented by the formula

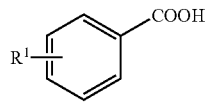

wherein $R^1$ is a straight or branched alkyl group having 3 to 15 carbon atoms or an ammonium salt or alkali metal salt of the compound, and a herbicide.

2. A phytotoxicity-controlling method which comprises applying the phytotoxicity-controlling composition described in claim 1 to a dry field for dry field cultivation of plants.

3. The phytotoxicity-controlling method described in claim 2 in which the herbicide in the phytotoxicity-controlling composition is an ammonium salt of imazaquin, dimethenamide-P, atrazine, flumetsulam, bispyribac salts, mesotrione, diflufenican, fenoxaprop-P-ethyl or a compound represented by the formula

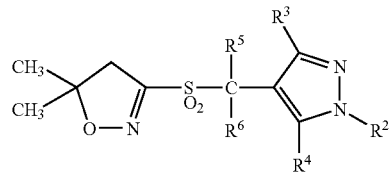

wherein $R^2$ is a hydrogen atom or an alkyl group having 1 to 10 carbon atoms, $R^3$ and $R^4$ are, each independently from the other, a halogen atom, an alkyl group having 1 to 10 carbon atoms, or a haloalkyl group or haloalkoxy group having 1 to 4 carbon atoms, and $R^5$ and $R^6$ are, each independently from the other, a hydrogen atom, a halogen atom, an alkyl group having 1 to 10 carbon atoms or a haloalkyl group having 1 to 4 carbon atoms.

4. The phytotoxicity-controlling method described in claim 2 in which the cultivated plants in the dry field are wheat, rye, barley, oats, Indian corn, sorghum, cotton, soybeans, adzuki beans, rapeseeds, beet or dry-paddy rice.

5. The phytotoxicity-controlling method described in claim 2 wherein the phytotoxicity-controlling composition comprises the benzoic acid compound or salt thereof and the herbicide in a mass proportion of 50:1 to 1:2.

6. The phytotoxicity-controlling composition described in claim 1, wherein the herbicide is an ammonium salt of imazaquin, dimethenamide-P, atrazine, flumetsulam, bispyribac salts, mesotrione, diflufenican, fenoxaprop-P-ethyl or a compound represented by the formula

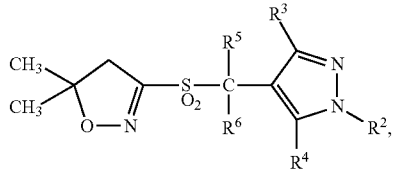

wherein $R^2$ is a hydrogen atom or an alkyl group having 1 to 10 carbon atoms, $R^3$ and $R^4$ are, each independently from the other, a halogen atom, an alkyl group having 1 to 10 carbon atoms, or a haloalkyl group or haloalkoxy group having 1 to 4 carbon atoms, and $R^5$ and $R^6$ are, each independently from the other, a hydrogen atom, a halogen atom, an alkyl group having 1 to 10 carbon atoms or a haloalkyl group having 1 to 4 carbon atoms.

7. The phytotoxicity-controlling composition described in claim 1, wherein a mass proportion of the benzoic acid compound or salt thereof and the herbicide is 50:1 to 1:2.

8. The phytotoxicity-controlling composition as described in claim 1, wherein the benzoic acid compound is a p-substituted benzoic acid wherein $R^1$ is a straight or branched chain alkyl group having 3 to 15 carbon atoms.

9. The phytotoxicity-controlling composition as described in claim 1, wherein the benzoic acid compound is a p-(tert-butyl) benzoic acid.

* * * * *